United States Patent
Sachidanadam

(10) Patent No.: US 11,000,715 B2
(45) Date of Patent: May 11, 2021

(54) MODULAR PORTABLE OXYGEN GENERATOR

(71) Applicant: O2-MATIC PRODUCTS PRIVATE LIMITED, Bangalore (IN)

(72) Inventor: John Paul Thambusami Joy Sachidanadam, Bangalore (IN)

(73) Assignee: O2-MATIC PRODUCTS PRIVATE LIMITED, Bangalore (IN)

(*) Notice: Subject to any disclaimer, the term of this patent is extended or adjusted under 35 U.S.C. 154(b) by 228 days.

(21) Appl. No.: 15/763,665

(22) PCT Filed: Feb. 20, 2017

(86) PCT No.: PCT/IN2017/000044
§ 371 (c)(1),
(2) Date: Mar. 27, 2018

(87) PCT Pub. No.: WO2017/141264
PCT Pub. Date: Aug. 24, 2017

(65) Prior Publication Data
US 2018/0345051 A1    Dec. 6, 2018

(30) Foreign Application Priority Data
Feb. 18, 2016   (IN) .............................. 201641005614

(51) Int. Cl.
*A62B 21/00*    (2006.01)
*A61M 16/16*    (2006.01)
(Continued)

(52) U.S. Cl.
CPC ........... *A62B 21/00* (2013.01); *A61M 16/101* (2014.02); *A61M 16/1005* (2014.02); *A61M 16/16* (2013.01); *F17C 1/00* (2013.01); *F17C 13/025* (2013.01); *A61M 2016/0027* (2013.01); *A61M 2202/0208* (2013.01); *A61M 2205/3389* (2013.01); *C01B 13/0211* (2013.01);
(Continued)

(58) Field of Classification Search
CPC ... A62B 21/00; A62B 7/08; F17C 1/00; F17C 2221/011; F17C 2270/025; A61M 16/101; C01B 13/0214
See application file for complete search history.

(56) References Cited

U.S. PATENT DOCUMENTS

| 5,725,834 A | 3/1998 | Nishii et al. | |
| 2009/0081115 A1* | 3/2009 | Ross | C01B 13/02 423/579 |

FOREIGN PATENT DOCUMENTS

WO    WO 1997010025 A1    3/1997

OTHER PUBLICATIONS

International Search Report of PCT Application No. PCT/IN2017/000044, dated Jun. 19, 2017.

\* cited by examiner

*Primary Examiner* — Margaret M Luarca
(74) *Attorney, Agent, or Firm* — Jason C. Cameron

(57) ABSTRACT

The various embodiments of the present invention disclose a modular portable oxygen generator including a reactor container having two vertical compartments, where one of the compartments houses a cartridge while another houses oxygen storage tank. The arrangement is provided with a mechanism to guide the oxygen generated in the cartridge after triggering to a defined outlet. The modular portable oxygen generator is light weight, easy to carry and easy to use with minimal maintenance as compared to heavy oxygen cylinders and generator.

11 Claims, 7 Drawing Sheets

(51) Int. Cl.
- *F17C 1/00* (2006.01)
- *A61M 16/10* (2006.01)
- *F17C 13/02* (2006.01)
- *A61M 16/00* (2006.01)
- *C01B 13/02* (2006.01)

(52) U.S. Cl.
CPC ...... *C01B 13/0214* (2013.01); *C01B 13/0218* (2013.01); *F17C 2221/011* (2013.01); *F17C 2270/025* (2013.01)

MODULAR PORTABLE OXYGEN GENERATOR

CROSS-REFERENCE TO RELATED APPLICATIONS

This application is a National Phase Application of PCT International Application No. PCT/IN2017/000044, International Filing Date Feb. 20, 2017, claiming priority of Indian Patent Application No. 201641005614, filed Feb. 18, 2016, which is hereby incorporated by reference in its entirety.

FIELD OF THE INVENTION

The present invention generally relates to oxygen generators. More particularly, the present invention relates to a portable and compact oxygen generator capable of producing the breathable oxygen on demand.

BACKGROUND OF THE INVENTION

Air is the most indispensable element for human life. Every living animal requires air for breathing and Oxygen is the most of important constituent of the air for the purposes of breathing. However, there are certain instances or places where the percentage of oxygen in air is very less to support functional breathing in a human. For example, the mountaineers find it difficult during mountain climbing as the amount of oxygen present in the air will be less. In another example, during deep sea diving, the diver will not be able to breath as the oxygen is not present in gaseous form or simply put there is no air to breath. Further, there are certain patients or people having met with accidents may not be able to breath and inhale the oxygen properly due their physical condition. Also during medical emergency situations where supplemental oxygen is mandatory. It is difficult or sometimes even not possible to carry those heavy oxygen cylinders while transferring patients or to mountains or under water etc. There are various instances where a person will face difficulty while carrying the presently used heavy oxygen cylinders.

Thus, to provide the oxygen to a user in a required manner, the oxygen can be produced and stored in oxygen cylinders and provided to the user when and where required. The oxygen production is done using metal cylinder with mechanical regulators to reduce the pressure to ambient levels, where even it is still in use. In all the aforementioned scenarios, carrying a heavy oxygen cylinder is not always a feasible option. The sheer weight of the oxygen cylinders limits the movement of the person who is carrying it along with him. Not only weight, but even refilling of the oxygen cylinders is a tedious task.

The present state of the art provides an alternative to the oxygen cylinders in the form of oxygen generator systems which are portable. The portable oxygen generating systems overcomes the problems of metal oxygen cylinders by providing oxygen in different situations where requirement for emergency oxygen arises. This helps in supplementing normal breathing. These are sometime only means available to generate oxygen to provide a high flow rate of breathable oxygen for an extended period.

So far, the known oxygen generating systems often require a user to mix a number of chemicals in a vessel. These systems typically cannot produce required flow of oxygen because of human error in mixing the reagents or because the reagents react too quickly or too slowly. Other known systems for generating oxygen involves reagents in a cartridge format often produce too little oxygen also tends to overheat reaction vessels. What it lacks is ease of use.

In view of the foregoing, there is a great need to reduce the apparatus's size, enhance its portability and thereby imparting flexibility in usage of the same. Further, there is a need for an apparatus that can generate oxygen at constant rate. Further, there is a need for an apparatus that can be easily refilled for subsequent uses. Also, during the refills or replacements the apparatus must continue to administer oxygen. Thus, there is need for an apparatus that solves these difficulties by minimizing the size of the apparatus making it very much compact, light-weight and portable as a kit style product.

The abovementioned shortcomings, disadvantages and problems are addressed herein and which will be understood by reading and studying the following specification.

SUMMARY OF THE INVENTION

The various embodiments of the present invention disclose a modular portable oxygen generator. The present invention solves the herein abovementioned difficulties by reducing the size of the oxygen generator making it very much compact, light-weight and portable as a kit style product.

According one embodiment of the present invention, the modular portable oxygen generator includes broadly includes a reactor container having two vertical compartments housing all other components/modules of the oxygen generator. First vertical compartment includes an opening at top end being configured to house a cartridge. A reactor enclosure, covering the opening at top end of the first vertical compartment, having an inward protrusion in center acting as a cartridge trigger for triggering release of oxygen in the cartridge. A cartridge slot followed by the opening at top end and a cartridge cover surrounding the cartridge. An opening at bottom or side or top of the first vertical compartment guarded by a hollow connector followed by an one-way valve for letting flow of oxygen released in the cartridge. A release ring attached to the hollow connector, where the release ring being pushed down to move the hollow connector. Second vertical compartment includes a storage tank to receive the oxygen released in the cartridge, a pressure gauge to maintain pressure of the oxygen to be released, a humidifier to humidify the oxygen to be released, and an outlet for the humidified oxygen. A pipe assembly connecting the hollow connector of the first vertical compartment and the storage tank. A base structure sealing bottom of the first vertical compartment and second vertical compartment.

According one embodiment of the present invention, the modular portable oxygen generator further includes an oxygen level indicator for indicating amount of oxygen left in the storage tank and showing user when to reload the next cartridge.

According one embodiment of the present invention, the modular portable oxygen generator further includes intuitive flow control means to ensure flow of oxygen from the outlet at a steady rate and pressure.

The foregoing has outlined, in general, the various aspects of the invention and is to serve as an aid to better understand the more complete detailed description which is to follow. In reference to such, there is to be a clear understanding that the present invention is not limited to the method or application of use described and illustrated herein. It is intended that any other advantages and objects of the present invention that become apparent or obvious from the detailed description or illustrations contained herein are within the scope of the present invention.

BRIEF DESCRIPTION OF THE ACCOMPANYING DRAWINGS

The other objects, features and advantages will occur to those skilled in the art from the following description of the preferred embodiment and the accompanying drawings in which.

Figure 1:
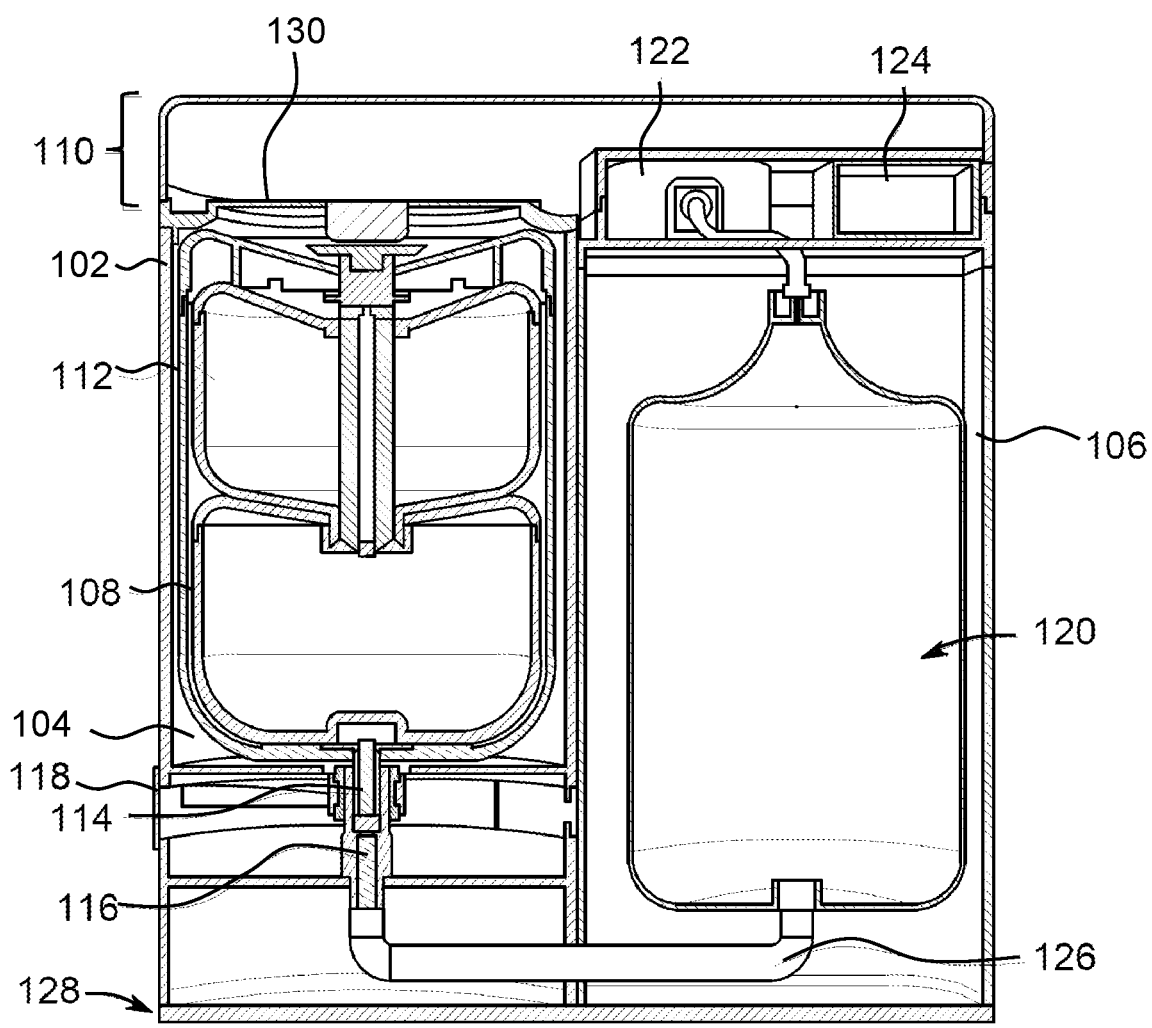
FIG. 1 is a schematic diagram illustrating a modular portable oxygen generator and arrangement of its components/modules, according to an embodiment of the present invention.

Although specific features of the present invention are shown in some drawings and not in others, this is done for convenience only as each feature may be combined with any or all of the other features in accordance with the present invention.

DETAILED DESCRIPTION OF THE INVENTION

In the following detailed description of the embodiments of the invention, reference is made to the accompanying drawings that form a part hereof, and in which are shown by way of illustration specific embodiments in which the invention may be practiced. These embodiments are described in sufficient detail to enable those skilled in the art to practice the invention, and it is to be understood that other embodiments may be utilized and that changes may be made without departing from the scope of the present invention. The following detailed description is, therefore, not to be taken in a limiting sense, and the scope of the present invention is defined only by the appended claims.

The specification may refer to "an", "one" or "some" embodiment(s) in several locations. This does not necessarily imply that each such reference is to the same embodiment(s), or that the feature only applies to a single embodiment. Single features of different embodiments may also be combined to provide other embodiments.

As used herein, the singular forms "a", "an" and "the" are intended to include the plural forms as well, unless expressly stated otherwise. It will be further understood that the terms "includes", "comprises", "including" and/or "comprising" when used in this specification, specify the presence of stated features, integers, steps, operations, elements and/or components, but do not preclude the presence or addition of one or more other features, integers, steps, operations, elements, components, and/or groups thereof. As used herein, the term "and/or" includes any and all combinations and arrangements of one or more of the associated listed items.

Unless otherwise defined, all terms (including technical and scientific terms) used herein have the same meaning as commonly understood by one of ordinary skill in the art to which this disclosure pertains. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The embodiments herein and the various features and advantages details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein can be practiced and to further enable those of skill in the art to practice the embodiments herein. Accordingly, the examples should not be construed as limiting the scope of the embodiments herein.

The present invention provides a modular portable oxygen generator, which is light weight, easy to carry and easy to use with minimal maintenance. The present design of the portable oxygen generator is a modification of the oxygen generator disclosed in the priority application. The entire design is based on the same concept of having a cartridge holding water and one or more chemicals separately. A mechanism of triggering the cartridge to start the reaction between water and one or more chemicals and thereby generating oxygen. A mechanism of guiding and releasing the generated oxygen at a required flow rate and pressure. The entire arrangement is modular so that the various parts can be manufactured separately and assembled together with ease.

The oxygen generator disclosed herein is capable to administering the oxygen at a steady pace during the time of changing of the cartridge also (please mention other new features also).

According to the present invention, the modular portable oxygen generator includes a reactor container having two vertical compartments, where one of the compartments houses a cartridge while another houses oxygen storage tank. The arrangement is provided with a mechanism to guide the oxygen generated in the cartridge after triggering to a defined outlet.

The schematic diagram of as given in FIG. 1 provides the detailed arrangement of the modular portable oxygen generator, according to the embodiment.

The reactor container 102 having first vertical compartment 104 and second vertical compartment 106. Where both the compartments are adjacently placed.

The first vertical compartment 104 includes an opening at top end configured to house a cartridge 108. Through this opening the cartridge 108 is loaded in the first vertical compartment 104. A reactor enclosure 110, covering the opening at top end of the first vertical compartment 104. The reactor enclosure 110 having an inward protrusion in its center acting as a cartridge trigger for triggering release of oxygen in the cartridge 108. The reactor enclosure is also designed to act as cartridge lock once the cartridge 108 is loaded. A cartridge slot followed by the opening at top end the first vertical compartment acting as a designated area compatible with shape of the cartridge to load the cartridge 108. A cartridge cover 112 which surrounds the loaded cartridge 108 acting as an insulator. An opening at bottom or side or top of the first vertical compartment guarded by a hollow connector 114 followed by an one-way valve 116 for letting flow of oxygen released in the cartridge 108. A release ring 118 attached to the hollow connector 114, where the release ring 118 can be pushed down to move the hollow connector (the mechanism of the release ring 118 and triggering of cartridge are described in later part).

The second vertical compartment 106 includes a storage tank 120 having an opening in its bottom to receive the oxygen released in the cartridge 108 and another opening at the top for release of oxygen stored inside it. A pressure gauge 122 connected via pipe to the opening at the top of the storage tank 120 to maintain release pressure of the oxygen stored in the storage tank 120. A humidifier 124 to humidify the oxygen to be released since the oxygen so released would be dry for breathing purposes. An outlet for the humidified oxygen. An opening is provided for allowing refill of water in the humidifier. In an embodiment; the outlet is connected to a pipe leading to a breathing mask which could be administered to a user.

There is a pipe assembly 126 connecting the hollow connector 114 (via one way valve 116) of the first vertical compartment 104 and the storage tank 120. The pipe assembly 126 receives the oxygen generated in the cartridge 108 and delivers it to the storage tank 120.

Bottom of the first vertical compartment 104 and second vertical compartment 106 is sealed by a common base structure 128, which may or may not be segmented.

Figure 2:
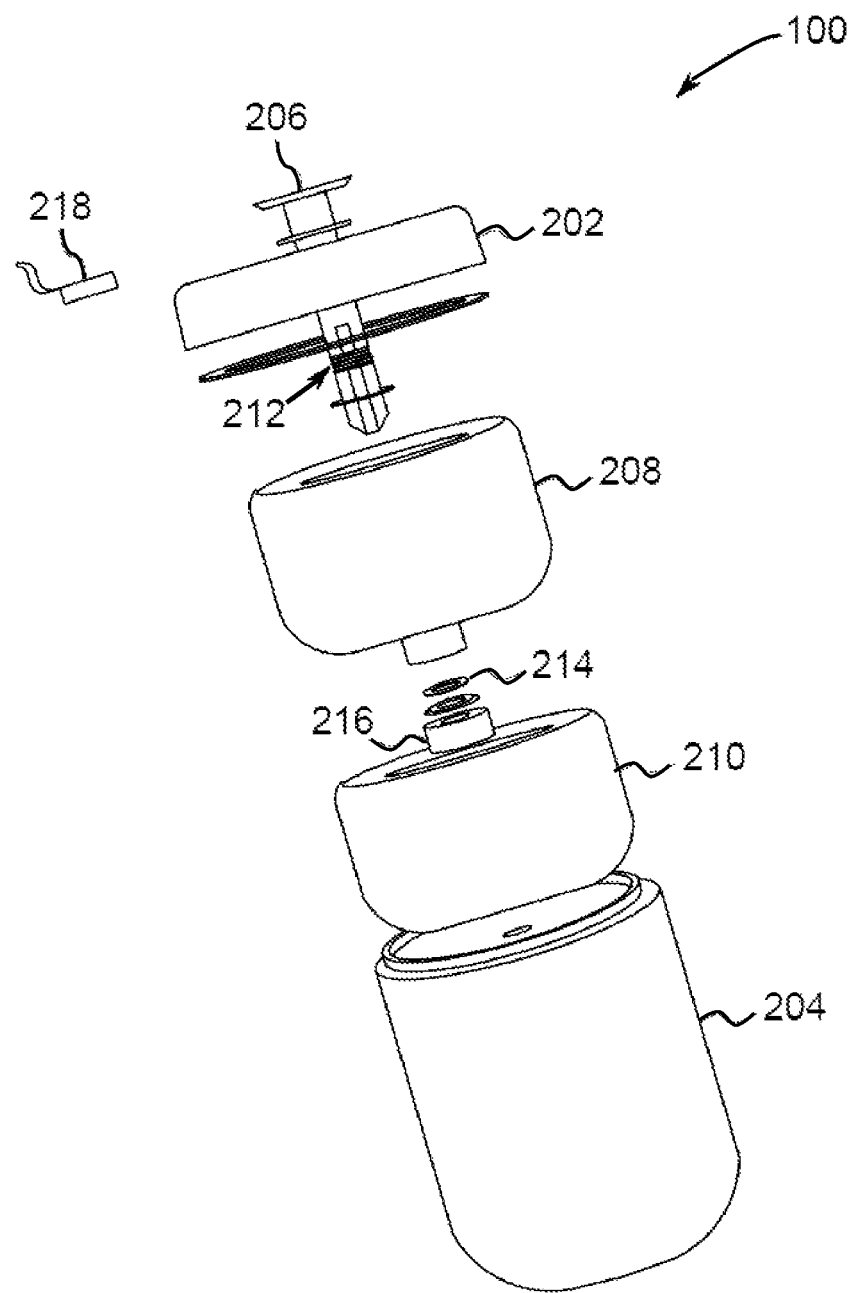
FIG. 2 is a schematic diagram illustrating exploded view of the cartridge, according to an embodiment of the present invention.
Figure 3:
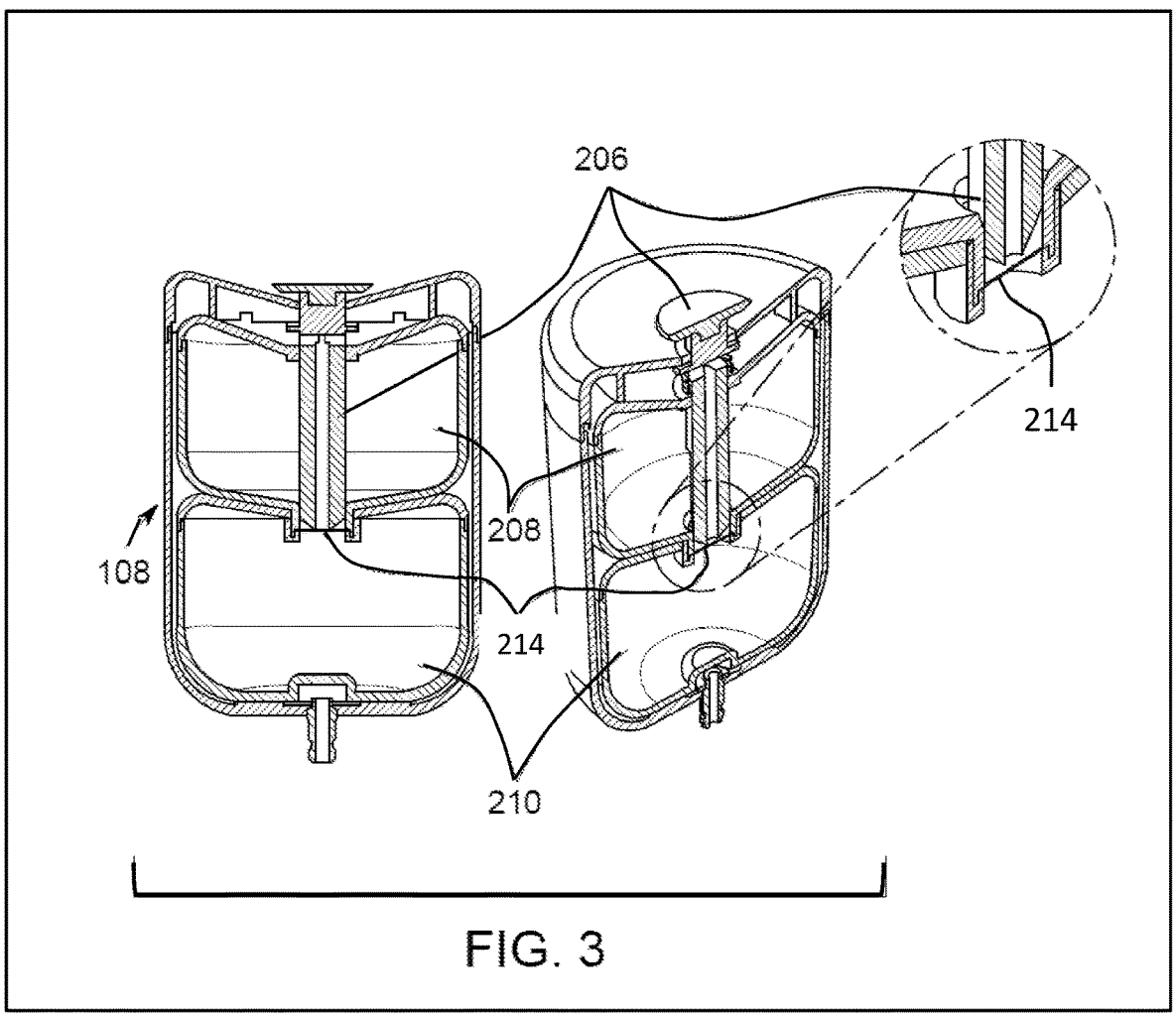
FIG. 3 is a schematic diagram illustrating vertical cross sectional view of the cartridge, according to an embodiment of the present invention.

The cartridge 108 used herein is one of the key components of oxygen generator 100. The schematic diagram of as given in FIG. 2 illustrates exploded view of detailed arrangement of parts of the cartridge 108, according to the embodiment. The FIG. 3 illustrates the vertical section view of the cartridge 108.

The cartridge 108 includes a cartridge cap 202 which has an opening in center and a cartridge outer shell 204 both fit together to form a closed elongate cartridge container. In one embodiment of the cartridge 108, a gasket is provided for tight fitting of the cartridge cap 202 and the cartridge outer shell 204. Below the cartridge cap 202 a water chamber 208 is positioned. The water chamber 208 is partially filled with water while having openings at top end and at bottom. Below the water chamber 208, a chemical chamber 210 having filled with one or more chemicals in sealed condition. The chemical chamber 210 has an opening at its top positioned below the bottom opening of the water chamber 208. A plunger 206 longitudinally slidably mounted in the cartridge 108. The plunger 206 mounted in such a way that it passes through the opening in the cartridge cap 202 reaches till bottom of the water chamber 208 while traversing through the opening at top end and bottom end of the water chamber 208. The plunger is sized to fit tightly in the openings so that preventing the seepage of water from the water chamber 208. The top portion of the plunger has a disc shape protruding out of the opening in the cartridge cap 202, where the disc is positioned just below the inward protrusion the reactor enclosure, thereby forming part of the cartridge triggering mechanism. The plunger 206 is hollow in center lengthwise till its top portion so that the oxygen produced in the chemical chamber could pass through the plunger. Therefore, the plunger also acts as a part of gas passage. One or more retraction means 212 is/are positioned at bottom portion of the plunger 206 for retracting the plunger 206 during triggering of the cartridge 108 and to enabling longitudinal slide of the plunger 206. In an embodiment of the cartridge 108, one or more springs are used as the retraction means 212. The cartridge is designed to have a gas passage (FIG. 7) for the release of the oxygen produced in the chemical chamber 210. The cartridge is also provided with a safety cap 218 placed below the disc shape protrusion of the plunger 206 and so as to avoid accidental triggering of the cartridge. Therefore, before triggering the cartridge the safety cap 218 has to be removed.

According to present invention, the cartridge is replaceable and refillable.

Figure 7:
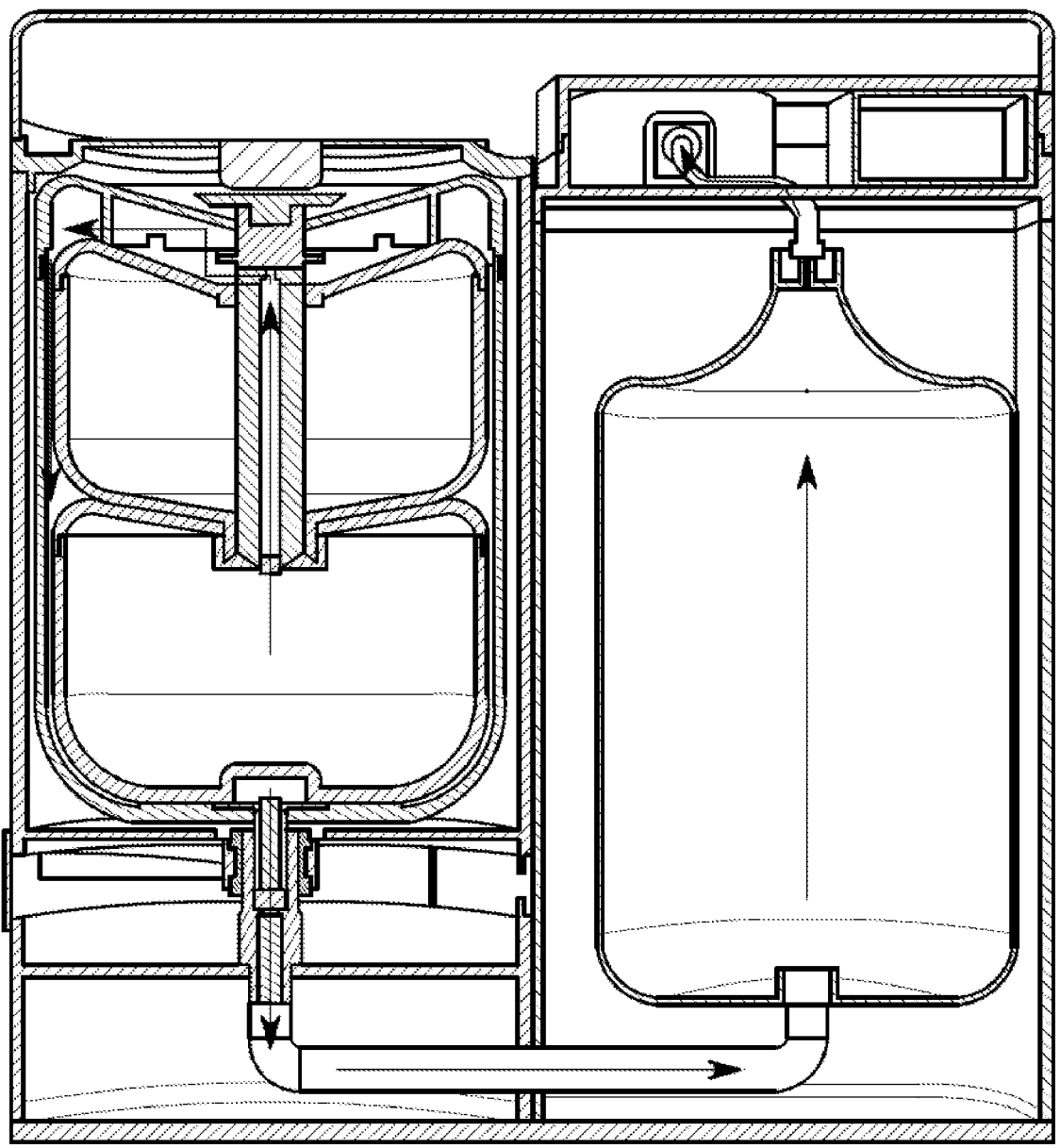
FIG. 7 illustrates the flow of the oxygen generated in the chemical chamber, according to an embodiment of the present invention.

In one embodiment, the gas passage for the release of the oxygen produced in the chemical chamber 210 includes the central hollow portion of the plunger 206 opening in the chemical chamber 210, gap between external diameter of water chamber 208 and internal diameter of the cartridge outer shell 204, extending to gap between external diameter of chemical chamber 210 and internal diameter of the cartridge outer shell 204, and opening on bottom of the cartridge outer shell 204 sealed by the hollow connector 114 guarded by one-way valve 116 (FIG. 7).

In an alternative embodiment, the gas passage for the release of the oxygen produced in the chemical chamber 210 includes the central hollow portion of the plunger 206 opening in the chemical chamber 210, gap between external diameter of water chamber 208 and internal diameter of the cartridge outer shell 204, extending to gap between external diameter of chemical chamber 210 and internal diameter of the cartridge outer shell 204, and an opening in cartridge outer shell 204 is on its side wall or top guarded by one-way valve (not shown in Figures). In this scenario, the connection point of the pipe assembly is adjusted to connect to the opening on side wall or top of cartridge outer shell.

Figure 4A:
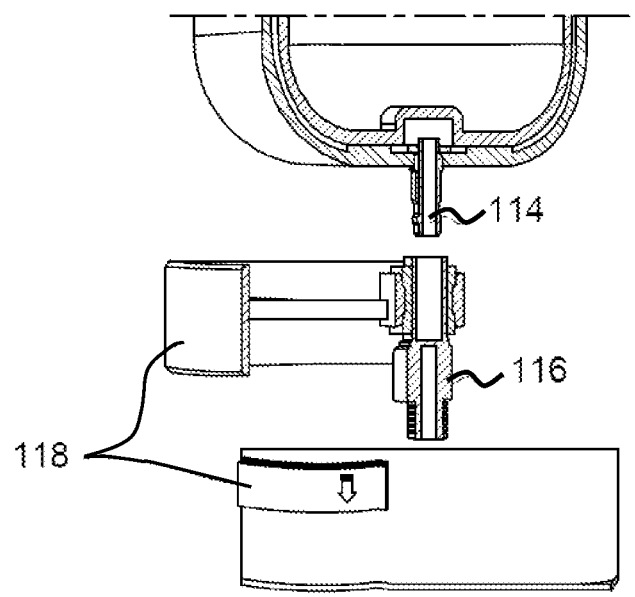
FIGS. 4A & 4B are schematic diagrams illustrating movement and function of the release ring attached to the hollow connector, according to an embodiment of the present invention.
Figure 4B:
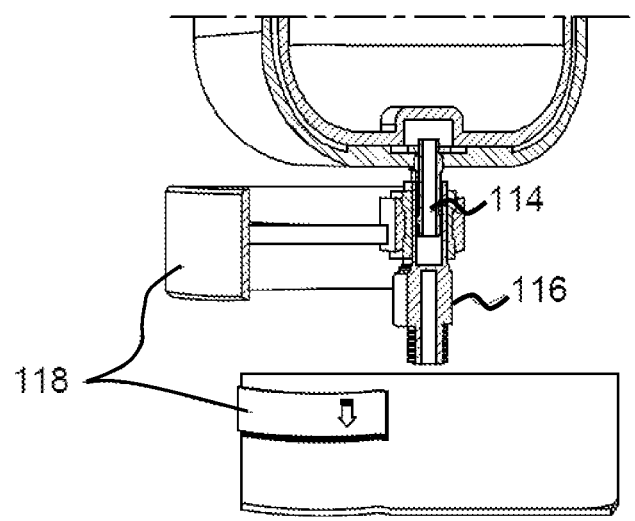

Movement and function of the release ring 118 attached to the hollow connector are illustrated in FIGS. 4A & 4B. The FIG. 4A depicts the condition when cartridge is unloaded, while FIG. 4B depicts when cartridge is loaded. During the loading of the cartridge 108, the bottom opening of the cartridge outer shell 204 locks in to the one-way valve 116 thereby allowing the flow of oxygen generated in the cartridge 108. The release ring 118 also locks the cartridge 108 when loaded and the release ring 118 being attached to the hollow connector 114 when moved down also releases the cartridge 118 so that next cartridge 108 can be loaded. Pressing cartridge into the cartridge slot locks the cartridge into first vertical compartment. Before inserting cartridge 108, release ring 118 will show red status as first vertical compartment 104 is empty or cartridge 108 is not inserted properly. After inserting cartridge the release ring will show status as green which means the modular portable oxygen generator is ready to use and cartridge is inserted properly.

Figure 5:
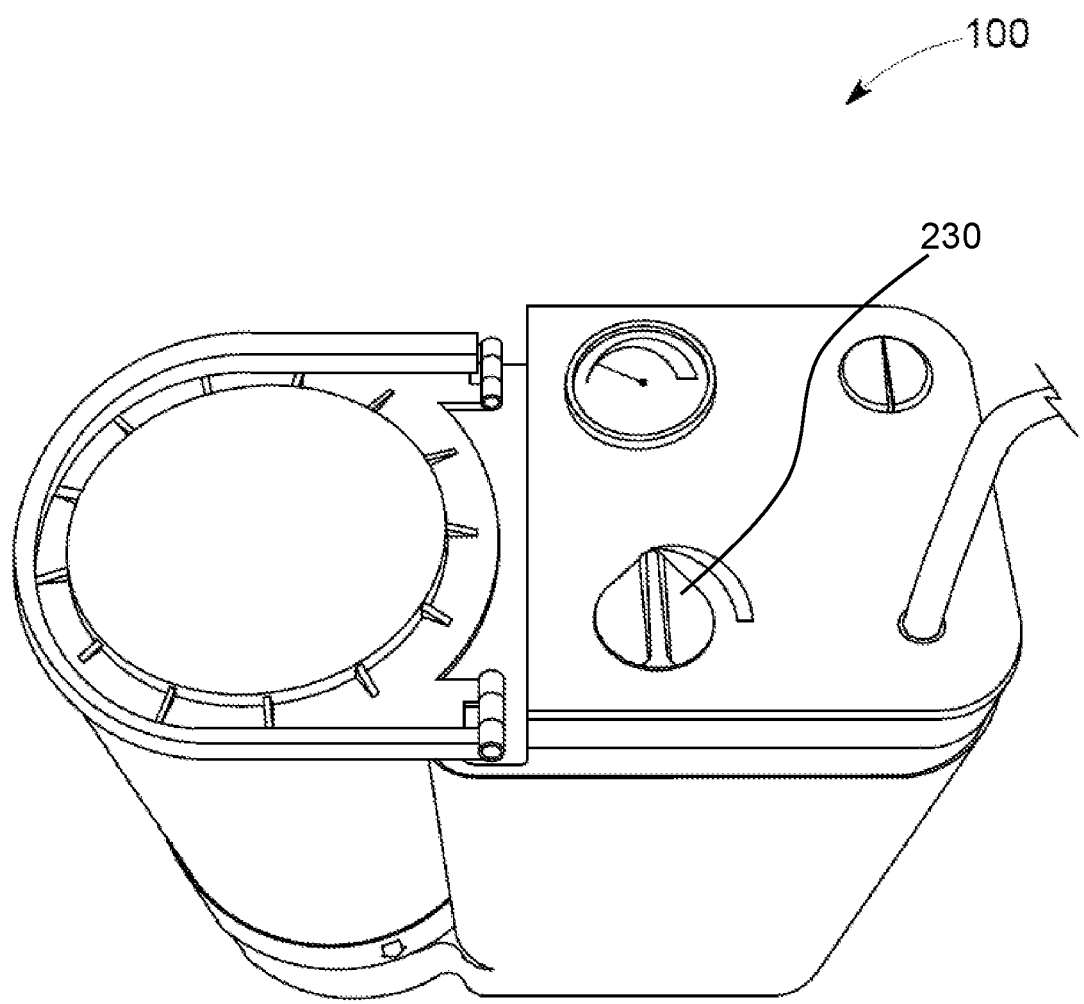
FIG. 5 is a perspective of the modular portable oxygen generator, according to an embodiment of the present invention.

In a further embodiment of the present invention, the modular portable oxygen generator 100 includes an oxygen level indicator for indicating amount of oxygen left in the storage tank and showing user when to reload the next cartridge. It may also include intuitive flow control means to ensure flow of oxygen from the outlet at a steady rate and pressure (FIG. 5).

In one of the embodiment of the present invention, the one or more chemicals filled in the chemical chamber 210 for generating oxygen are selected from a group sodium percarbonate, potassium superoxide, peroxide species (hydrogen peroxide), urea-hydrogen peroxide and percarbamide peroxide. Preferably, the chemical may be sodium percarbonate. The sodium percarbonate naturally decomposes, very slowly, to form sodium carbonate and hydrogen peroxide. The hydrogen peroxide further decomposes to form water and oxygen and liberate some heat (exothermic reaction). The chemical reaction is as follows:

$$2Na_2CO_3 \cdot 3H_2O_2 \rightarrow 2Na_2CO_3 + 3H_2O + 1.5O_2 + Heat$$

The one or more chemicals used herein could be in the form of granular powder or pellets or powder in a porous pouch or candle stick or combination thereof.

According another embodiment of the present invention, any of the other suitable catalyst may also be used to generate oxygen in a controlled rate, without departing from the scope of the invention.

According to the present invention, the one or more chemical and the water can be taken in predefined ratios for optimum generation of oxygen.

Trigger Mechanism of the Cartridge

Figure 6A:
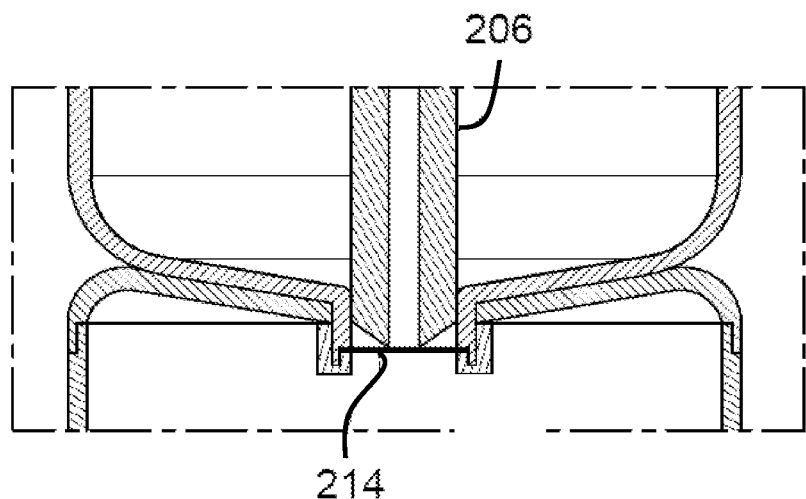
FIG. 6A depicts the initial condition of the plunger when it has not pierced the film and FIG. 6B depicts the pierced condition, according to an embodiment of the present invention.
Figure 6B:
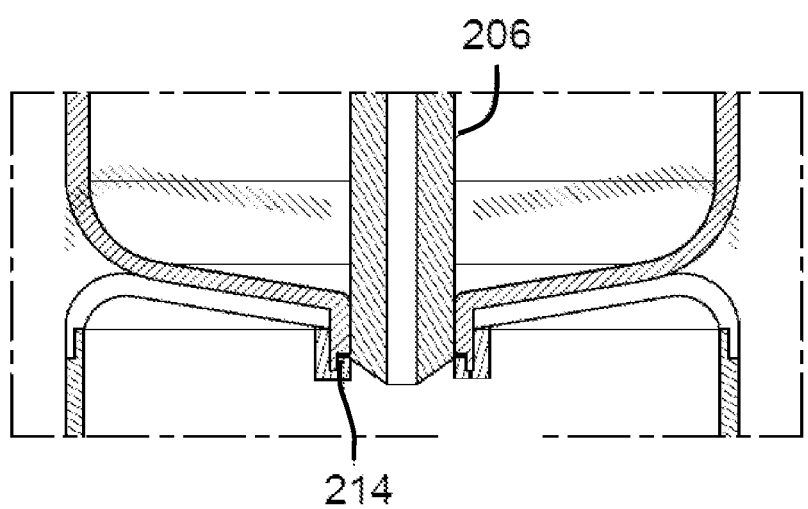

The safety cap 218 is removed from the cartridge 108 and loaded in the cartridge slot. The reactor enclosure 110 is closed to lock the cartridge 108 inside. The closing of the reactor enclosure 110 presses the top portion of the plunger 206 having a disc shape, which leads to piercing of the film 214 thereby allowing water to flow from water chamber 208 to chemical chamber and eventually react with the one or more chemicals generating oxygen. The FIG. 6A depicts the initial condition of the plunger 206 when it has not pierced the film 214, while FIG. 6B depicts the pierced condition.

The FIG. 7 illustrates the flow of the oxygen generated in the chemical chamber according to an embodiment of the present invention. The direction of flow is depicting by arrows, which starts from the gas passage leading to the storage tank via pipe assembly and finally exiting through the outlet.

The present invention is advantageous for being able to maintain continuous administration of oxygen from the storage tank even during reloading of the cartridges.

According to the present invention, mechanism in the first vertical compartment 104 does not allow the cartridge 108 to be removed until all the oxygen produced inside the cartridge 108 is collected in the storage tank 120.

According to the present invention, once the storage tank 120 in the second vertical compartment 106 is maxed with oxygen, the mechanism does not allow further loading of cartridges in the first vertical compartment 104.

According to an embodiment of the present invention, structure of the modular portable oxygen generator and its components can be made up of non-reactive, non-corrosive materials such as, but not limited to, plastic, silicon, and the like.

The present embodiments have been described with reference to specific example embodiments; it will be evident that various modifications and changes may be made to these embodiments without departing from the broader spirit and scope of the various embodiments.

I claim:

1. A modular portable oxygen generator, comprising:
a reactor container having a first vertical compartment and a second vertical compartment, wherein the first vertical compartment comprises:
an opening at a top end;
a cartridge configured to be housed in the first vertical compartment via the opening at the top end;
a reactor enclosure, covering the opening at the top end of the first vertical compartment, and having an inward protrusion in a center configured to act as a cartridge trigger for triggering release of oxygen in the cartridge;
a cartridge slot configured to contain the cartridge and aligned with the opening at the top end;
a cartridge cover surrounding the cartridge;
an opening at one of a bottom, side, and top of the first vertical compartment guarded by a hollow connector and a one-way valve for allowing a flow of oxygen released in the cartridge; and
a release ring attached to the hollow connector, wherein the release ring is configured to be pushed down to move the hollow connector, and wherein the second vertical compartment comprises:
a storage tank configured to receive the oxygen released in the cartridge;
a pressure gauge configured to verify the functioning of the cartridge;
a humidifier configured to humidify the oxygen to be released; and
an outlet for the humidified oxygen;
a pipe assembly configured to connect the hollow connector of the first vertical compartment and the storage tank; and
a base structure configured to seal the bottom of the first vertical compartment and second vertical compartment.

2. The modular portable oxygen generator as claimed in claim 1, wherein the release ring is configured to lock the cartridge when the cartridge is loaded, and wherein when the release ring is moved down, the release ring is configured to release the cartridge so that the next cartridge can be loaded.

3. The modular portable oxygen generator as claimed in claim 1, further comprising a bottom of a cartridge outer shell configured to lock into the one-way valve during loading, thereby allowing a flow of oxygen generated in the cartridge.

4. The modular portable oxygen generator as claimed in claim 1, wherein the cartridge comprises:
a cartridge cap having an opening in a center and a cartridge outer shell fitting together to form a closed elongate cartridge container, wherein the cartridge outer shell has an opening corresponding to the opening at a bottom of the first vertical compartment;
a water chamber, having an opening at the top end and an opening at the bottom;
a chemical chamber being filled with one or more chemicals in a sealed condition, having an opening positioned below the bottom opening of the water chamber;
a plunger longitudinally slidably mounted in the cartridge, passing through the opening in the cartridge cap and extending to the bottom of the water chamber while traversing through the opening at the top end and the bottom end of the water chamber, wherein
the plunger is configured to fit tightly in the openings, and wherein
the top portion of the plunger having a disc shape protruding out of the opening in the cartridge cap, and wherein
the disc is positioned below the inward protrusion of the reactor enclosure, and wherein
to the plunger having a hollow center extending lengthwise to the top portion
retraction means for the plunger positioned at the bottom portion of the plunger to enable longitudinal sliding of the plunger;

a gas passage for the release of the oxygen produced in the chemical chamber; and a safety cap placed below the disc shape protrusion of the plunger so as to avoid accidental triggering of the cartridge.

5. The modular portable oxygen generator as claimed in claim 4, wherein the one or more chemicals are selected from a group consisting of sodium percarbonate, potassium superoxide, peroxide species (hydrogen peroxide), urea-hydrogen peroxide, and percarbamide peroxide.

6. The modular portable oxygen generator as claimed in claim 4, wherein the one or more chemicals used herein being in the form of one of a granular powder, pellets, powder in a pouch, and a candle stick.

7. The modular portable oxygen generator as claimed in claim 4, wherein the gas passage for the release of the oxygen produced in the chemical chamber comprises:

the central hollow portion of the plunger opening in the chemical chamber;

a first gap between an external diameter of a water chamber and an internal diameter of the cartridge container, extending to a second gap between an external diameter of the chemical chamber and the internal diameter of the cartridge outer shell; and an opening on the bottom of the cartridge outer shell sealed by the hollow connector.

8. The modular portable oxygen generator as claimed in claim 1 wherein when the reactor enclosure is closed, the reactor enclosure is configured to place a downward force on the top portion of a plunger having a disk shape, thereby piercing a firm and allowing water to flow from a water chamber to a chemical chamber, and wherein the water reacts with one or more chemicals to generate oxygen.

9. The modular portable oxygen generator as claimed in claim 1, further comprises an oxygen level indicator configured to indicate an amount of oxygen left in the storage tank and indicate to a user when to reload the next cartridge.

10. The modular portable oxygen generator as claimed in claim 1, further comprising an intuitive flow control means to allow flow of oxygen from the outlet at a steady rate and pressure.

11. The modular portable oxygen generator as claimed in claim 1, wherein the cartridge is replaceable and refillable.

* * * * *